US011779281B2

(12) United States Patent
Adachi et al.

(10) Patent No.: US 11,779,281 B2
(45) Date of Patent: Oct. 10, 2023

(54) EVALUATION SYSTEM EVALUATION DEVICE, AND BIOLOGICAL INFORMATION ACQUISITION DEVICE

(71) Applicant: Sharp Kabushiki Kaisha, Osaka (JP)

(72) Inventors: Yoshihisa Adachi, Sakai (JP); Yuki Edo, Sakai (JP); Rieko Ogawa, Sakai (JP); Ryota Tomizawa, Sakai (JP); Tetsuya Okumura, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 647 days.

(21) Appl. No.: 16/980,472

(22) PCT Filed: Feb. 21, 2019

(86) PCT No.: PCT/JP2019/006646
§ 371 (c)(1),
(2) Date: Sep. 14, 2020

(87) PCT Pub. No.: WO2019/181356
PCT Pub. Date: Sep. 26, 2019

(65) Prior Publication Data
US 2021/0015430 A1 Jan. 21, 2021

(30) Foreign Application Priority Data

Mar. 20, 2018 (JP) ................................. 2018-053225

(51) Int. Cl.
*A61B 5/00* (2006.01)
*G16H 40/67* (2018.01)
(Continued)

(52) U.S. Cl.
CPC .............. *A61B 5/721* (2013.01); *A61B 5/742* (2013.01); *G16H 40/67* (2018.01); *G16H 50/70* (2018.01);
(Continued)

(58) Field of Classification Search
CPC . A61B 5/721; A61B 5/742; A61B 2560/0247; G16H 40/67;
(Continued)

(56) References Cited

U.S. PATENT DOCUMENTS

2005/0277817 A1 12/2005 Eda
2009/0203972 A1 8/2009 Heneghan et al.
(Continued)

FOREIGN PATENT DOCUMENTS

JP 2003-337102 A 11/2003
JP 2005-160783 A 6/2005
(Continued)

OTHER PUBLICATIONS

Official Communication issued in International Patent Application No. PCT/JP2019/006646, dated May 14, 2019.

*Primary Examiner* — Jonathan T Kuo
(74) *Attorney, Agent, or Firm* — KEATING & BENNETT, LLP (57) ABSTRACT

Performance of a biological information acquisition device of a non-contact type is appropriately evaluated. An evaluation system evaluating a first biological information acquisition device of a non-contact type includes a first body movement suppressing unit that suppresses body movement of a first region, a first body movement detecting unit that detects a first body movement amount, which indicates a magnitude of the body movement of the first region, in a non-contact manner, and a second biological information acquisition device different from the first biological information acquisition device. The evaluation system outputs validity information which indicates that an evaluation result of the first biological information acquisition device is valid, in a case where the first body movement amount is equal to or less than a first threshold.

20 Claims, 7 Drawing Sheets

(51) Int. Cl.
  *G16H 50/70* (2018.01)
  *A61B 5/021* (2006.01)
  *A61B 5/024* (2006.01)
  *A61B 5/08* (2006.01)
  *A61B 5/145* (2006.01)
  *A61B 5/16* (2006.01)

(52) U.S. Cl.
  CPC ............... *A61B 5/021* (2013.01); *A61B 5/024* (2013.01); *A61B 5/0816* (2013.01); *A61B 5/14542* (2013.01); *A61B 5/165* (2013.01); *A61B 2560/0247* (2013.01)

(58) Field of Classification Search
  CPC ....... G06T 7/0012–7/0016; G06T 7/20–7/292; G06T 2207/30004–2207/30104; G06T 2207/30196–2207/30201
  See application file for complete search history.

(56) References Cited

U.S. PATENT DOCUMENTS

| | | |
|---|---|---|
| 2011/0009718 A1 | 1/2011 | Gavish |
| 2014/0163343 A1 | 6/2014 | Heneghan et al. |
| 2016/0100766 A1 | 4/2016 | Yoshioka et al. |
| 2019/0021607 A9 | 1/2019 | Deneghan et al. |
| 2021/0038087 A1 | 2/2021 | Heneghan et al. |

FOREIGN PATENT DOCUMENTS

| | | |
|---|---|---|
| JP | 2009-538720 A | 11/2009 |
| JP | 2011-509733 A | 3/2011 |
| JP | 2016-077890 A | 5/2016 |
| JP | 2016-106894 A | 6/2016 |
| KR | 10-2011-0037202 A | 4/2011 |

EVALUATION SYSTEM EVALUATION DEVICE, AND BIOLOGICAL INFORMATION ACQUISITION DEVICE

TECHNICAL FIELD

The disclosure below relates to an evaluation system that evaluates a biological information acquisition device of a non-contact type.

BACKGROUND ART

Various techniques by which biological information of a living body (e.g., a human) is acquired (measured) have been proposed. For example, PTL 1 discloses a technique by which a brain activity function of a subject is measured in a non-contact manner.

CITATION LIST

Patent Literature

PTL 1: Japanese Unexamined Patent Application Publication No. 2003-337102

SUMMARY OF INVENTION

Technical Problem

An aspect of the present disclosure aims to appropriately evaluate performance of a biological information acquisition device of a non-contact type.

Solution to Problem

In order to solve the aforementioned problem, an evaluation system according to an aspect of the present disclosure is an evaluation system evaluating a first device that is a biological information acquisition device of a non-contact type, the first device acquires a first measurement value, which indicates biological information of a living body, by measuring a first region of the living body in a non-contact manner, the evaluation system includes: a first body movement suppressing unit that suppresses body movement of the first region; a first body movement detecting unit that detects a first body movement amount, which indicates a magnitude of the body movement of the first region, in the non-contact manner; and a second device that is a biological information acquisition device different from the first device, the second device acquires a second measurement value, which indicates the biological information, by measuring a second region of the living body, and the evaluation system further includes: a comparison unit that compares the first measurement value and the second measurement value; an evaluation unit that evaluates the first device based on a result of the comparison of the comparison unit; and an evaluation determination unit that, in a case where the first body movement amount is equal to or less than a first threshold, outputs validity information which indicates that an evaluation result of the first device from the evaluation unit is valid.

Moreover, in order to solve the aforementioned problem, an evaluation device according to an aspect of the present disclosure is an evaluation device included in an evaluation system evaluating a first device that is a biological information acquisition device of a non-contact type, the first device acquires a first measurement value, which indicates biological information of a living body, by measuring a first region of the living body in a non-contact manner, the evaluation system further includes a first body movement suppressing unit that suppresses body movement of the first region, a first body movement detecting unit that detects a first body movement amount, which indicates a magnitude of the body movement of the first region, in the non-contact manner, and a second device that is a biological information acquisition device different from the first device, the second device acquires, in the evaluation system, a second measurement value, which indicates the biological information, by measuring a second region of the living body, and the evaluation device includes: a comparison unit that compares the first measurement value and the second measurement value; an evaluation unit that evaluates the first device based on a result of the comparison of the comparison unit; and an evaluation determination unit that, in a case where the first body movement amount is equal to or less than a first threshold, outputs validity information which indicates that an evaluation result of the first device from the evaluation unit is valid.

Advantageous Effects of Invention

According to an evaluation system according to an aspect of the present disclosure, it is possible to appropriately evaluate performance of a biological information acquisition device of a non-contact type. Moreover, a similar effect is exerted also by an evaluation device according to an aspect of the present disclosure.

DESCRIPTION OF EMBODIMENTS

Embodiment 1

An evaluation system 1 of Embodiment 1 will be described below in detail. For convenience of description, a member having the same function as that of a member described in Embodiment 1 will be given the same reference sign in each of the following embodiments, and description thereof will not be repeated.

(Outline of Evaluation System 1)

Figure 1:
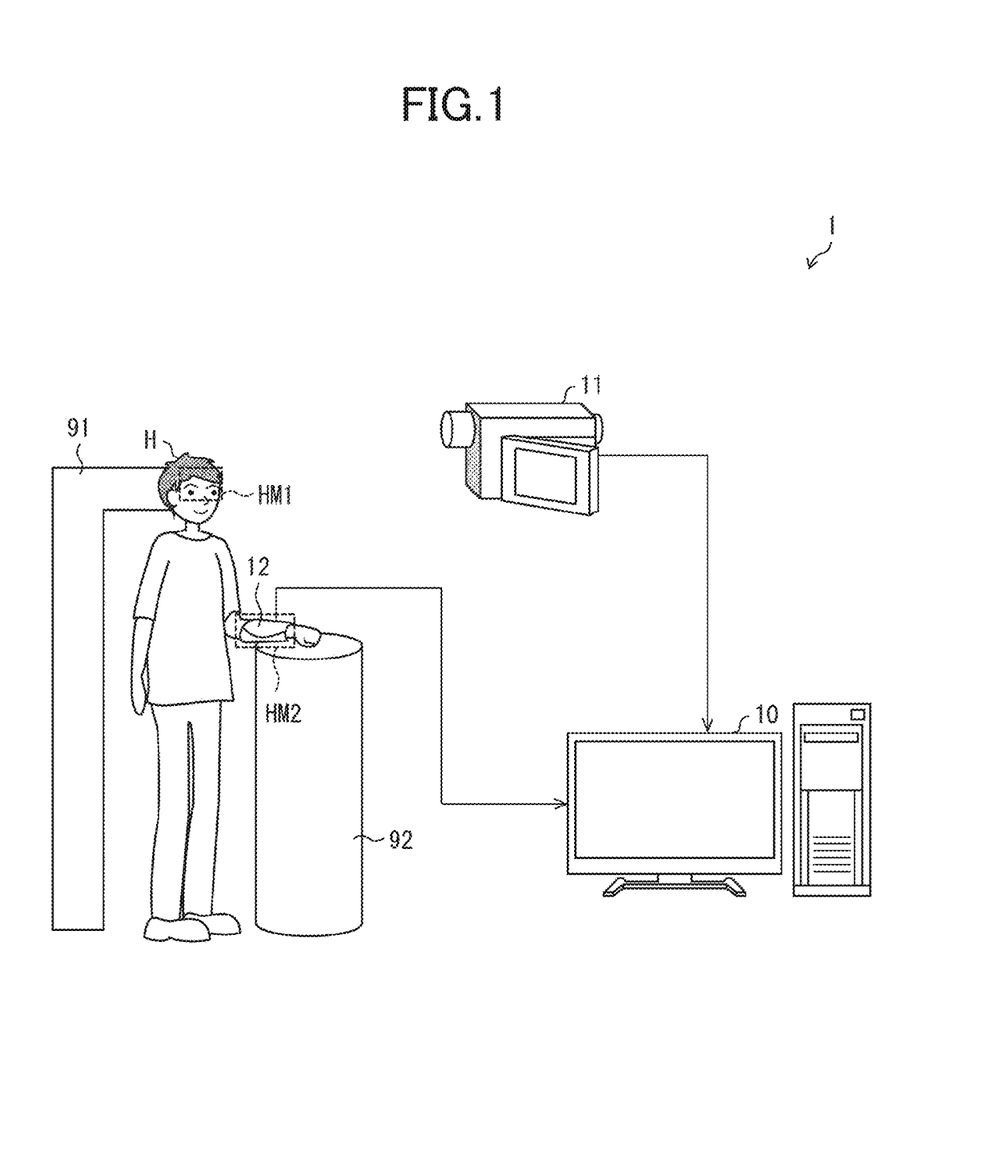
FIG. 1 is a view illustrating an outline of an evaluation system of Embodiment 1.

FIG. 1 is a view illustrating an outline of the evaluation system 1. The evaluation system 1 (specifically, an evaluation device 10 described below) evaluates performance of a first biological information acquisition device 11 (first device). The evaluation system 1 includes the evaluation device 10, a second biological information acquisition device 12 (second device), a first body movement suppressing unit 91, and a second body movement suppressing unit 92.

The first biological information acquisition device 11 is a biological information acquisition device of a non-contact type. The first biological information acquisition device 11 acquires biological information of a subject H (living body) in a non-contact manner. In Embodiment 1, a case where the living body is a human is exemplified. Note that the living body in an aspect of the present disclosure is not limited to a human. The living body may be any living body as long as biological information thereof is able to be acquired by each of the first biological information acquisition device 11 and the second biological information acquisition device 12. Accordingly, the living body may be an animal, for example, a dog or a cat.

Figure 2:
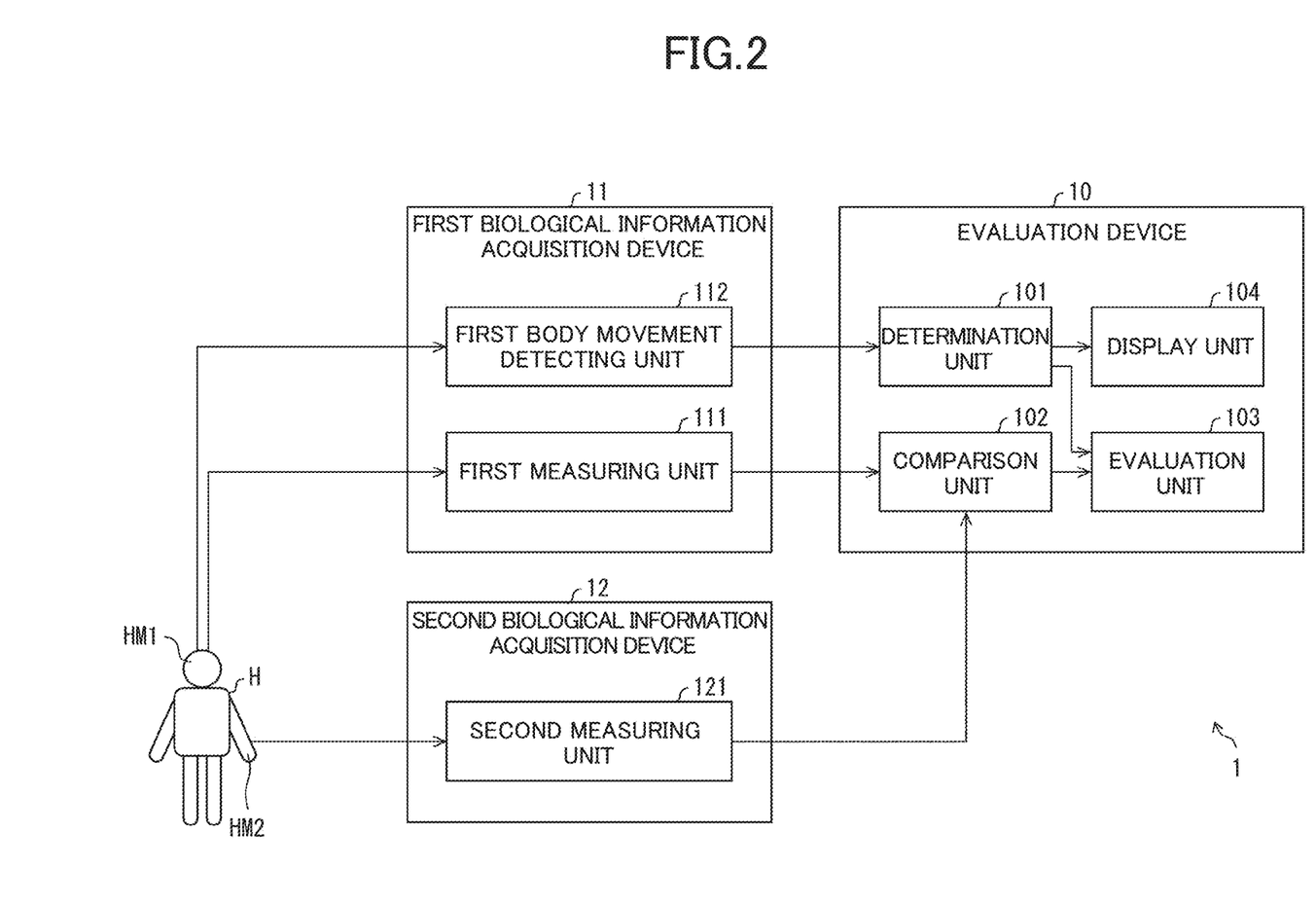
FIG. 2 is a functional block diagram illustrating a configuration of a main part of the evaluation system of FIG. 1.

FIG. 2 is a functional block diagram illustrating a configuration of the evaluation system 1. The first biological information acquisition device 11 is, for example, a camera (image capturing device) that is able to photograph at least a part of a region of a body of the subject H. The first biological information acquisition device 11 includes a first measuring unit 111 and a first body movement detecting unit 112.

In Embodiment 1, for convenience, a case where the first body movement detecting unit 112 is provided in the first biological information acquisition device 11 is exemplified. However, the first body movement detecting unit 112 may be provided outside of the first biological information acquisition device 11. It is sufficient that the first body movement detecting unit 112 is provided as a component of the evaluation system 1.

The first measuring unit 111 measures a first region HM1 (predetermined region) of the subject H in a non-contact manner to thereby acquire a first measurement value (hereinafter, M1) which indicates biological information. In Embodiment 1, the first region HM1 is a face of the subject H.

For example, the first biological information acquisition device 11 photographs the subject H and generates a moving image in which an image of the face of the subject H is represented. The first measuring unit 111 analyzes the moving image by using a known algorithm to thereby acquire M1. For example, the first measuring unit 111 analyzes the image of the face of the subject H, which is included in each frame of the moving image, and acquires M1. In Embodiment 1, the first biological information acquisition device 11 acquires a blood pressure value of the subject H as the biological information. Therefore, the first measuring unit 111 acquires, as M1, a numerical value which indicates the blood pressure value of the subject H.

The first body movement detecting unit 112 detects a first body movement amount (hereinafter, D1), which indicates the magnitude of body movement of the first region HM1, in a non-contact manner. For example, the first body movement detecting unit 112 analyzes the moving image by using a known algorithm to thereby acquire D1.

There is a possibility that accuracy in measuring the biological information is degraded in a case where the body movement of the subject H is great. Thus, the first measuring unit 111 may correct the numerical value, which indicates the blood pressure value of the subject H, on the basis of D1. In this case, the first measuring unit 111 outputs the numerical value subjected to the correction as M1 (measurement result). It is thereby possible to provide a measurement result in which the influence of the body movement of the subject H is reduced.

The second biological information acquisition device 12 measures a second region HM2 (predetermined region) of the subject H to thereby acquire biological information. For example, the second region HM2 is an arm (e.g., a left arm) of the subject H. The second biological information acquisition device 12 is a biological information acquisition device different from the first biological information acquisition device 11. Specifically, the second biological information acquisition device 12 is a biological information acquisition device as a reference for the first biological information acquisition device 11. Accordingly, the kind of biological information acquired by the second biological information acquisition device 12 is the same as the kind of biological information acquired by the first biological information acquisition device 11.

The second biological information acquisition device 12 includes a second measuring unit 121. The second biological information acquisition device 12 measures the second region HM2 to thereby acquire a second measurement value (hereinafter, M2) which indicates the biological information (blood pressure value). M2 is a numerical value as a reference of M1. Accordingly, it is preferable that the evaluation system 1 be configured so as to be able to measure M2 with high accuracy by using the second biological information acquisition device 12.

In Embodiment 1, a case where the second biological information acquisition device 12 is a biological information acquisition device of a contact type is exemplified. For example, the second biological information acquisition device 12 is an electronic sphygmomanometer with a cuff. Note that a mercury-type electronic sphygmomanometer may also be used as the second biological information acquisition device 12. In addition, a wristwatch-type measuring device may also be used as the second biological information acquisition device 12.

The first body movement suppressing unit 91 suppresses body movement of the first region HM1. For example, the first body movement suppressing unit 91 is a structure (e.g., a columnar structure) that is able to support at least a part of the first region HM1. For example, the first body movement suppressing unit 91 supports an occipital region of the subject H. When the first body movement suppressing unit 91 is provided, it is possible to reduce D1, so that accuracy in measuring M1 is able to be improved.

The second body movement suppressing unit 92 suppresses body movement of the second region HM2. For example, the second body movement suppressing unit 92 is a structure (e.g., an armrest) that supports at least a part of the second region HM2. When the second body movement suppressing unit 92 is provided, it is possible to reduce a second body movement amount (D2 described below) which indicates the magnitude of the body movement of the second region HM2, so that accuracy in measuring M2 is able to be improved.

The evaluation device 10 includes a determination unit 101 (evaluation determination unit), a comparison unit 102, an evaluation unit 103, and a display unit 104. For convenience, a case where the display unit 104 is provided in the evaluation device 10 is exemplified in Embodiment 1. However, the display unit 104 may be provided outside of the evaluation device 10. It is sufficient that the display unit 104 is provided as a component of the evaluation system 1.

The determination unit 101 acquires D1 from the first body movement detecting unit 112. The determination unit 101 compares D1 and a given first threshold (hereinafter, TH1) in a magnitude relationship. The determination unit 101 determines an evaluation result from the evaluation unit 103 on the basis of the magnitude relationship. Furthermore, the determination unit 101 may control the evaluation unit 103 on the basis of the magnitude relationship.

When, for example, $D1 \leq TH1$ is satisfied (when the first body movement amount is equal to or less than the first threshold), the body movement of the first region HM1 is considered to be relatively small. It is therefore expected that M1 is able to be acquired relatively accurately. When, for example, $D1 \leq TH1$ is satisfied, the determination unit 101 may cause the evaluation unit 103 to evaluate the first biological information acquisition device 11. That is, the determination unit 101 permits the evaluation unit 103 to evaluate the first biological information acquisition device 11.

On the other hand, when $D1 > TH1$ is satisfied (when the first body movement amount is larger than the first threshold), the body movement of the first region HM1 is considered to be relatively great. Therefore, there is a concern that accuracy of M1 is lower than that of a case of $D1 \leq TH1$. Then, when, for example, $D1 > TH1$ is satisfied, the determination unit 101 may cause the evaluation unit 103 to stop evaluation of the first biological information acquisition device 11. That is, the determination unit 101 does not permit the evaluation unit 103 to evaluate the first biological information acquisition device 11.

Note that the determination unit 101 may cause the evaluation unit 103 to evaluate the first biological information acquisition device 11 additionally when $D1 > TH1$ is satisfied. When, for example, $D1 > TH1$ is satisfied, the determination unit 101 may cause the evaluation unit 103 to evaluate the first biological information acquisition device 11 and, furthermore, may output information (invalidity information) indicating that the evaluation result from the evaluation unit 103 is invalid. The determination unit 101 may output the invalidity information to any functional unit. For example, the determination unit 101 outputs the invalidity information to the evaluation unit 103. The same also applies to validity information which will be described below.

In this manner, it is sufficient that the determination unit 101 is set so as to make the evaluation result from the evaluation unit 103 invalid when $D1 > TH1$ is satisfied. Processing for "causing the evaluation unit 103 to stop evaluation of the first biological information acquisition device 11" in the description above is an example of processing of the determination unit 101 when the evaluation result from the evaluation unit 103 is regarded as invalid.

On the other hand, when $D1 \leq TH1$ is satisfied, the determination unit 101 may cause the evaluation unit 103 to evaluate the first biological information acquisition device 11 and may then output information (validity information) indicating that the evaluation result from the evaluation unit 103 is valid. In this manner, it is sufficient that the determination unit 101 is set so as to make the evaluation result from the evaluation unit 103 valid when $D1 \leq TH1$ is satisfied. "Causing the evaluation unit 103 to evaluate the first biological information acquisition device 11" in the description above is an example of processing of the determination unit 101 when the evaluation result from the evaluation unit 103 is regarded as valid.

The determination unit 101 may output at least one of the invalidity information and the validity information to the display unit 104. For example, the display unit 104 displays the invalidity information, which is supplied from the determination unit 101, as predetermined image data (e.g., a character or an object). The same also applies to the validity information. Thereby, it is possible to cause a user to visually identify validity (or invalidity) of the evaluation result.

It is possible to say that the invalidity information is information whose priority to be reported to the user is higher than that of the validity information. This is because, when the evaluation result is invalid, the first biological information acquisition device 11 is considered not to satisfy predetermined performance as described later. Therefore, it is preferable that at least the invalidity information be displayed on the display unit 104 in the evaluation system 1.

Furthermore, neither the invalidity information nor the validity information is necessarily reported visually. For example, a speaker (sound output unit) which is not illustrated may be provided in the evaluation system 1. The determination unit 101 may output the invalidity information to the speaker, for example. When the invalidity information is supplied from the determination unit 101, the speaker outputs a beep. As above, it is also possible to cause the user to auditorily identify the invalidity information (indicating that the evaluation result is invalid).

It is sufficient that the evaluation system 1 is provided with a reporting unit that reports at least one of the invalidity information and the validity information to the user. Each of the display unit 104 and the sound output unit is an example of the reporting unit. Moreover, the display unit 104 and the sound output unit may be combined to constitute a single reporting unit as a whole.

Note that the first body movement amount (D1) is not limited to an amount which directly indicates the magnitude of the body movement of the first region HM1. For example, the first body movement detecting unit 112 may analyze the moving image in which the image of the face of the subject H is represented and may follow (track) the body movement of the first region HM1 in the moving image. Then, the first body movement detecting unit 112 may acquire, as D1, an evaluation indicator (e.g., a following error) indicating following processing performance. Additionally with such a method, the first body movement detecting unit 112 is able to detect D1 in a non-contact manner. Note that a known algorithm may be used for each of the following processing and a method of calculating the evaluation indicator. In a case of the present example, when D1 is equal to or less than the first threshold (TH1), it is considered that the first region HM1 is able to be followed and that the influence of the body movement of the first region HM1 is relatively small. Thus, also in the present example, when $D1 \leq TH1$ is satisfied, the determination unit 101 may cause the evaluation unit 103 to evaluate the first biological information acquisition device 11 as described above.

Hereinafter, a predetermined condition which is related to a body movement amount and under which the evaluation result of the first biological information acquisition device 11 from the evaluation unit 103 is regarded as valid is also generically referred to as a body movement condition. A condition of $D1 \leq TH1$ is an example of the body movement condition. In Embodiment 1, the body movement condition is used additionally as a condition under which the evaluation unit 103 is permitted to evaluate the first biological information acquisition device 11. The same also applies to each of the following embodiments.

As above, when it is considered inappropriate for the evaluation unit 103 to perform evaluation of the first biological information acquisition device 11 (when the body movement condition is not satisfied), the determination unit 101 regards the evaluation result from the evaluation unit 103 as invalid. In this case, the determination unit 101 does not permit evaluation of the first biological information acquisition device 11 by the evaluation unit 103.

Only when it is considered appropriate for the evaluation unit 103 to perform evaluation of the first biological information acquisition device 11 (when the body movement condition is satisfied), the determination unit 101 regards the evaluation result from the evaluation unit 103 as valid. As above, the determination unit 101 is able to determine the validity of the evaluation result from the evaluation unit 103. Therefore, the determination unit 101 is able to selectively cause the evaluation unit 103 to perform evaluation.

The comparison unit 102 acquires M1 and M2 from the first measuring unit 111 and the second measuring unit 121, respectively. The comparison unit 102 compares M1 and M2 and outputs a comparison result to the evaluation unit 103. In Embodiment 1, the comparison unit 102 compares M1 and M2 by calculating a difference between M1 and M2. For example, the comparison unit 102 calculates R=M1−M2. The comparison unit 102 outputs this R to the evaluation unit 103 as the comparison result.

Note that the comparison unit 102 may compare M1 and M2 by performing a mathematical operation different from that of the aforementioned example. For example, the comparison unit 102 may compare M1 and M2 by calculating a value of a ratio of M1 and M2. For example, the comparison unit 102 calculates R=M1/M2. The comparison unit 102 outputs this R to the evaluation unit 103 as the comparison result.

The evaluation unit 103 evaluates the first biological information acquisition device 11 (specifically, the performance of the first biological information acquisition device 11) on the basis of R (comparison result from the comparison unit 102). For example, in a case of R=M1−M2, when |R|≈0 is satisfied, it is possible to say that a relationship of M1≈M2 is established. That is, it is expected that the first biological information acquisition device 11 is able to acquire the biological information with accuracy close to that of the second biological information acquisition device 12 (the biological information acquisition device as the reference).

Then, when, for example, |R|≤THR, the evaluation unit 103 (performs evaluation and) determines that the first biological information acquisition device 11 is able to appropriately acquire the biological information. That is, the evaluation unit 103 determines that the first biological information acquisition device 11 satisfies the predetermined performance. Note that THR is a given threshold for |R|.

On the other hand, when a relationship of |R|≈0 is not established, it is possible to say that M1 is significantly different from M2. That is, it is considered that the first biological information acquisition device 11 fails to acquire the biological information with accuracy close to that of the second biological information acquisition device 12. Then, when |R|>THR is satisfied, the evaluation unit 103 determines that the first biological information acquisition device 11 fails to appropriately acquire the biological information. That is, the evaluation unit 103 determines that the first biological information acquisition device 11 does not satisfy the predetermined performance.

(Example of Acquiring Timing of First Biological Information Acquisition Device and Second Biological Information Acquisition Device)

Figure 3:
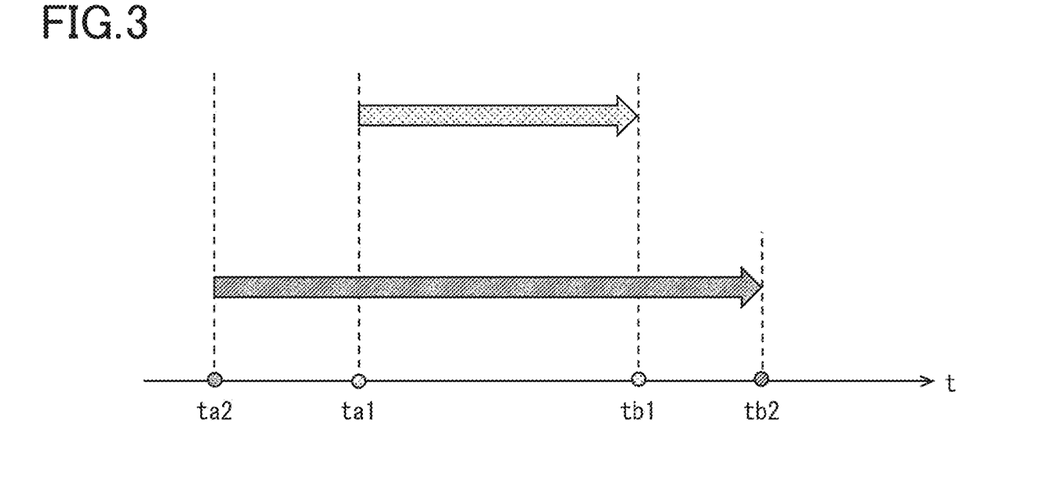
FIG. 3 is a view illustrating an example of acquiring timing of biological information by a first biological information acquisition device and a second biological information acquisition device.

FIG. 3 is a timing chart illustrating an example of acquiring timing of the biological information by using the first biological information acquisition device 11 and the second biological information acquisition device. In FIG. 3, t is a sign indicating time (time point). Note that any of time ta1 to tb2 described below may be set by the evaluation device 10.

In the biological information acquisition device 11, (i) a start time of acquisition (measurement of M1) of the biological information by the first measuring unit 111 is set as the time ta1, and (ii) an end time of the acquisition of the biological information by the first measuring unit 111 is set as the time tb1. The time ta1 is also referred to as a first measurement start time (first measurement start time point). Moreover, the time tb1 is also referred to as a first measurement end time (first measurement end time point).

A period during which ta1≤t≤tb1 is satisfied is referred to as a first measurement period. The first biological information acquisition device 11 acquires M1 at least once during the first measurement period. In Embodiment 1, for simplification, the first biological information acquisition device 11 is to acquire M1 once during the first measurement period.

In the second biological information acquisition device 12, (i) a start time of acquisition (measurement of M2) of the biological information by the second measuring unit 121 is set as the time ta2, and (ii) an end time of the acquisition of the biological information by the second measuring unit 121 is set as the time tb2. The time ta2 is also referred to as a second measurement start time (second measurement start time point). Moreover, the time tb2 is also referred to as a second measurement end time (second measurement end time point).

A period during which ta2≤t≤tb2 is satisfied is referred to as a second measurement period. The second biological information acquisition device 12 acquires M2 at least once during the second measurement period. In Embodiment 1, for simplification, the second biological information acquisition device 12 is to acquire M2 once during the second measurement period.

From a viewpoint of comparison of M1 and M2, ideally, it is also considered that the first measurement period and the second measurement period are preferably coincident with each other. That is, ideally, it is also considered that each time is preferably set so that ta1=ta2 and tb1=tb2 are satisfied. However, actually, the first measurement period and the second measurement period are not necessarily set to be completely coincident with each other. This is because a time required for acquiring the biological information may differ between the first biological information acquisition device 11 and the second biological information acquisition device 12.

In Embodiment 1, it is preferable that setting be performed so that at least a part of the first measurement period overlaps the second measurement period. This is because, as long as both the first biological information acquisition device 11 and the second biological information acquisition device 12 are able to measure the subject H in the same state during at least the part of the period, it is possible to cause the second biological information acquisition device 12 to adequately function as the reference for the first biological information acquisition device 11.

In the example of FIG. 3, setting is performed so that (i) ta2<ta1 and (ii) tb1<tb2 are satisfied. That is, (i) the second measurement start time is set as the time before the first measurement start time, and (ii) the second measurement end time is set as the time after the first measurement end time.

That is, in the example of FIG. 3, setting is performed so that a whole of the first measurement period overlaps the second measurement period. When the first measurement period and the second measurement period are set in this manner, the second biological information acquisition device 12 is able to measure the subject H during a period including the whole of the first measurement period. It is therefore possible to enhance reliability of the second biological information acquisition device 12 as the reference. As a result, it is possible to enhance the precision of the evaluation of the first biological information acquisition device 11.

Note that the first measurement period may be set so as not to overlap the second measurement period. This is because, when the second biological information acquisition device 12 whose reliability is inspected in advance is used, the second biological information acquisition device 12 functions as the reference also in such a case.

(Effect)

Generally, measurement accuracy of a biological information acquisition device of a non-contact type is significantly influenced by body movement of the subject H. Therefore, for the biological information acquisition device to appropriately acquire biological information, various methods of reducing the influence of body movement of the subject H have been adopted. However, the methods generally differ between kinds of biological information acquisition devices of the non-contact type.

On the basis of this point, inventors of the present application (hereinafter, inventors) have devised that "it is necessary to set a common (constant) reference condition which does not depend on the kind of the first biological information acquisition device 11 (biological information acquisition device of a non-contact type) to appropriately evaluate the performance of the first biological information acquisition device 11". On the basis of the idea, the inventors have considered a configuration of the evaluation system 1. According to the evaluation system 1, it is possible to provide the common reference condition.

For example, in the evaluation system 1, it is possible to suppress the body movement of the first region HM1 by using the first body movement suppressing unit 91. Then, only when $D1 \leq TH1$ is satisfied (when the body movement of the first region HM1 is relatively small), the evaluation result from the evaluation unit 103 is regarded as valid. That is, only when it is expected that measurement accuracy of the first biological information acquisition device 11 is relatively high, it is possible to treat the evaluation result from the evaluation unit 103 as a valid one. Accordingly, for example, only when it is expected that the measurement accuracy of the first biological information acquisition device 11 is relatively high, it is possible to evaluate the first biological information acquisition device 11.

In this manner, according to the evaluation system 1, it is possible to determine the validity of the evaluation result from the evaluation unit 103 under the common reference condition. Accordingly, it is possible to evaluate the performance of the first biological information acquisition device 11 under the common reference condition, for example. That is, it is possible to appropriately evaluate the performance of the first biological information acquisition device 11 differently from a conventional one. For example, according to the evaluation system 1, it is possible to appropriately evaluate whether or not the first biological information acquisition device 11 satisfies a predetermined required performance.

Furthermore, in the evaluation system 1, setting is performed so that at least a part of the first measurement period overlaps the second measurement period. It is therefore possible to reliably cause the second biological information acquisition device 12 to function as the reference for the first biological information acquisition device 11. Thus, it is also possible to improve reliability of the comparison result from the comparison unit 102.

Modified Example (1) The biological information according to an aspect of the present disclosure is not limited to a blood pressure value. Other examples of the biological information include heart rate, pulse rate, pulse wave, respiratory frequency, percutaneous arterial blood oxygen saturation ($SpO_2$), stress levels, and the like. The biological information may be any information (indicator) indicating a physiological state of a living body. It is sufficient that the biological information is information which is able to be acquired by each of the first biological information acquisition device 11 and the second biological information acquisition device 12.

(2) In Embodiment 1, a case where the first biological information acquisition device 11 is the camera and the second biological information acquisition device 12 is the electronic sphygmomanometer with a cuff is exemplified. Therefore, in Embodiment 1, a case where the first region HM1 is the face of the subject H and the second region HM2 is the arm of the subject H is exemplified. Note that the first region HM1 and the second region HM2 may be respectively set in accordance with specifications of the first biological information acquisition device 11 and the second biological information acquisition device 12.

For example, the first biological information acquisition device 11 may be any kind of biological information acquisition device of the non-contact type which is able to acquire the biological information. For example, a microwave sensor that measures oscillation of a body surface of the subject H may be used as the first biological information acquisition device 11. Accordingly, it is also possible to set a region (e.g., the chest or abdomen) other than the face of the subject H as the first region HM1.

Similarly, the second biological information acquisition device 12 may also be any kind of biological information acquisition device. For example, the second biological information acquisition device 12 may be a measuring device which is attachable to a fingertip. That is, it is also possible to set a region (e.g., a fingertip) other than the arm of the subject H as the second region HM2.

(3) In Embodiment 1, a case where one first biological information acquisition device 11 is evaluated is exemplified. However, in the evaluation system 1, after one first biological information acquisition device 11 is evaluated, it is also possible to replace the first biological information acquisition device 11 with a different kind of first biological information acquisition device (a biological information acquisition device of the non-contact type). In the evaluation system 1, it is possible to evaluate the different first biological information acquisition device as long as the common reference condition is satisfied.

In addition, a plurality of first biological information acquisition devices 11 may be evaluated by the evaluation system 1 at the same time. In this case, none of the plurality of first biological information acquisition devices 11 are required to be evaluated individually (one by one), it is possible to shorten a time required for evaluating the plurality of first biological information acquisition devices 11.

Note that the evaluation device 10 may record information indicating a measurement environment of the first biological information acquisition device 11. For example, the evaluation device 10 may record information indicating temperature, humidity, date and time, or the like at a time of measurement of the first biological information acquisition device 11. By referring to this information, it is possible to evaluate the performance of the first biological information acquisition device 11 in consideration of the influence of the measurement environment.

When, for example, the plurality of first biological information acquisition devices 11 are evaluated at the same time, measurement environments are almost the same. Therefore, it is possible to evaluate variations of performance between the plurality of first biological information acquisition devices 11.

On the other hand, when one first biological information acquisition device 11 is evaluated plural times, a measurement environment may vary in accordance with measuring timing. Thus, it is possible to evaluate the influence of the measurement environment on the performance of the one first biological information acquisition device 11.

(4) In Embodiment 1, a case where the comparison unit 102 is caused to compare M1 and M2 once and the first biological information acquisition device 11 is thereby evaluated is exemplified. However, the comparison unit 102 may be caused to compare M1 and M2 plural times and the first biological information acquisition device 11 may thereby be evaluated.

For example, the first biological information acquisition device 11 acquires M1 N times (N is an integer of 2 or more) during the first measurement period. Similarly, the second biological information acquisition device 12 acquires M2 N times during the second measurement period. In this case, the comparison unit 102 acquires M1 and M2 N times. Then, the comparison unit 102 calculates R each time M1 and M2 are acquired. That is, the comparison unit 102 calculates R N times. Hereinafter, N items of R calculated by the comparison unit 102 are represented as R1, R2, . . . , and RN.

Next, the comparison unit 102 calculates a statistic of R1 to RN. The comparison unit 102 outputs the statistic to the evaluation unit 103 as the comparison result. For example, the comparison unit 102 calculates an average value (hereinafter, Rm) of R1 to RN as the statistic. The comparison unit 102 outputs Rm to the evaluation unit 103 as the comparison result. The evaluation unit 103 performs processing similar to that of Embodiment 1 by using Rm acquired from the comparison unit 102.

In this manner, by causing the comparison unit 102 to perform statistical processing by which the statistic is calculated, it is possible to reduce the influence of a measurement error of each of M1 and M2. Therefore, it is possible to further improve reliability of the evaluation result of the first biological information acquisition device 11. Note that the statistical processing is not limited only to the processing by which the average value is calculated. The comparison unit 102 may calculate the statistic by other known statistical processing.

Figure 4:
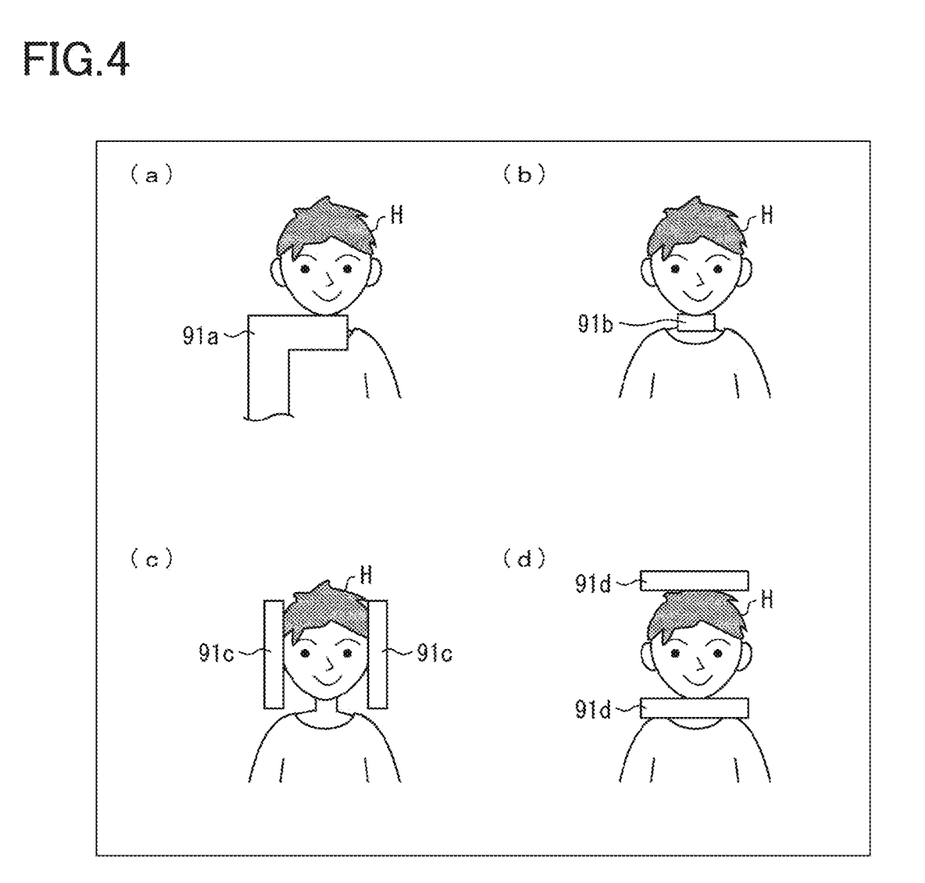
FIGS. 4(a) to 4(d) are views by each of which a modified example of a first body movement suppressing unit is explained.

(5) A configuration of the first body movement suppressing unit 91 is not limited to the example of FIG. 1. FIG. 4 is a view for explaining modified examples of the first body movement suppressing unit 91. Hereinafter, first body movement suppressing units of FIGS. 4(a) to 4(d) are referred to as first body movement suppressing units 91a to 91d, respectively. In the examples of FIG. 4, the first region HM1 is the face of the subject H similarly to that of the example of FIG. 1.

As illustrated in FIG. 4(a), the first body movement suppressing unit 91a supports the jaw of the subject H. As illustrated in FIG. 4(b), the first body movement suppressing unit 91b fixes the neck of the subject H. As illustrated in FIG. 4(c), the first body movement suppressing units 91c hold the head of the subject H therebetween in a horizontal direction. As illustrated in FIG. 4(d), the first body movement suppressing units 91d hold the head of the subject H therebetween in a vertical direction. Note that the first body movement suppressing unit 91c and the first body movement suppressing unit 91d may be used in combination.

The body movement of the first region HM1 is able to be suppressed additionally by the first body movement suppressing units 91a to 91d of FIG. 4, similarly to the first body movement suppressing unit 91. As above, it is sufficient that the first body movement suppressing unit is in contact with a region near the face of the subject H at least one place.

(6) The evaluation system 1 may be further provided with a member (first fixation member) that fixes the first biological information acquisition device 11. By providing the first fixation member, movement of the first biological information acquisition device 11 is able to be suppressed, so that it is possible to improve the measurement accuracy of the first biological information acquisition device 11.

However, the first fixation member is not necessarily required to be provided. When, for example, the first biological information acquisition device 11 is a device (e.g., a smartphone) which is able to be handheld by the subject H, the first fixation member may be omitted. For example, a case where a smartphone acquires the biological information in a state where the user holds the smartphone is considered. In this case, movement of the smartphone is suppressed by the user's hand. Thus, it is possible to omit the first fixation member.

Note that, depending on the case, it is preferable that the first biological information acquisition device 11 be evaluated intentionally without providing the first fixation member. For example, a case in which it is desirable to check the extent to which the movement of the first biological information acquisition device 11 influences the measurement accuracy of the first biological information acquisition device 11 may be considered. In such a case, it is preferable that the first fixation member not be provided. By performing the aforementioned check, it is possible to evaluate the extent to which the first biological information acquisition device 11 exhibits performance (e.g., camera shaking correction performance of a smartphone) by which the influence of the movement of the first biological information acquisition device 11 itself is offset.

Modified Example

Differently from Embodiment 1, the second biological information acquisition device 12 may be a biological information acquisition device of the non-contact type. For example, a biological information acquisition device of the same kind (e.g., a camera) as that of the first biological information acquisition device 11 is able to be used as the second biological information acquisition device 12. When performance (reliability) of a biological information acquisition device of the non-contact type has been inspected in advance, the biological information acquisition device of the non-contact type is able to be used as the second biological information acquisition device 12.

Hereinafter, the second biological information acquisition device 12 of the non-contact type is also referred to as a second biological information acquisition device of the non-contact type. On the other hand, the second biological information acquisition device 12 of the contact type is also referred to as a second biological information acquisition device of the contact type.

When the second biological information acquisition device of the contact type is used, the second region HM2 is covered and hidden by the second biological information acquisition device in many cases. Accordingly, it is difficult to measure the second region HM2 itself and a region near the second region HM2 by the first biological information acquisition device 11. Therefore, when the second biological information acquisition device of the contact type is used, the first region HM1 and the second region HM2 are required to be set as regions apart from each other.

On the other hand, when the second biological information acquisition device of the non-contact type is used, the second region HM2 is not covered or hidden by the second biological information acquisition device. Therefore, the first region HM1 and the second region HM2 are able to be set as regions close to each other. Furthermore, the first region HM1 is able to be set in the identical region to the second region HM2. For example, the face of the subject H is able to be set as both the first region HM1 and the second region HM2.

By setting the first region HM1 in a region close to the second region HM2 or in the identical region, it is possible to further improve reliability of M2 as the reference. Thus, it is possible to further improve the reliability of the evaluation result of the first biological information acquisition device 11.

In addition, by setting the first region HM1 in the region close to the second region HM2 or in the identical region, it is possible to use the first body movement suppressing unit 91 and the second body movement suppressing unit 92 as a common member. Therefore, it is possible to reduce the number of parts of the evaluation system 1.

Note that the "region" of the identical region means a region of the subject H, for example, the face, the chest, the abdomen, an upper arm, or the fingertip. Neither measurement positions nor measurement areas of the first biological information acquisition device 11 and the second biological information acquisition device 12 necessarily exactly coincide, as long as being within the identical region. That is, the identical region is a region in which equivalent measurement results are able to be obtained by the first biological information acquisition device 11 and the second biological information acquisition device 12 even when the measurement positions (measurement areas) do not exactly coincide.

For example, as described above, a case where the face of the subject H is set as the "identical region" is considered. In this case, the first region HM1 may be a left side of a forehead from a center, and the second region HM2 may be a right side of the forehead from the center. Alternatively, the first region HM1 may be the forehead, and the second region HM2 may be a cheek. In such cases, it is possible to say that the first region HM1 and the second region HM2 are in the identical region (region which is included in the face and in which equivalent measurement results are able to be obtained).

Furthermore, the "close region" means a region which is not regarded as the "identical region" to a certain region but is in a vicinity of the certain region. For example, in a case where the first region HM1 is the face, when the second region HM2 is the neck, it is possible to say that the first region HM1 and the second region HM2 are regions close to each other. Alternatively, in a case where the second region HM2 is the neck, when the first region HM1 is the chest, it is possible to say that the first region HM1 and the second region HM2 are regions close to each other.

Modified Example

Differently from Embodiment 1, it is also possible to remove the second body movement suppressing unit 92 from the evaluation system 1. That is, it should be noted that the second body movement suppressing unit 92 is not an essential component for the evaluation system 1.

For example, the second biological information acquisition device 12 may be configured to acquire M2 by offsetting the influence of the body movement of the second region HM2, similarly to the first biological information acquisition device 11. In this case, even when the second body movement suppressing unit 92 is removed from the evaluation system 1, the second biological information acquisition device 12 is able to acquire highly accurate M2. Therefore, the first biological information acquisition device 11 may be evaluated by the evaluation system 1 which does not include the second body movement suppressing unit 92.

Embodiment 2

Figure 5:
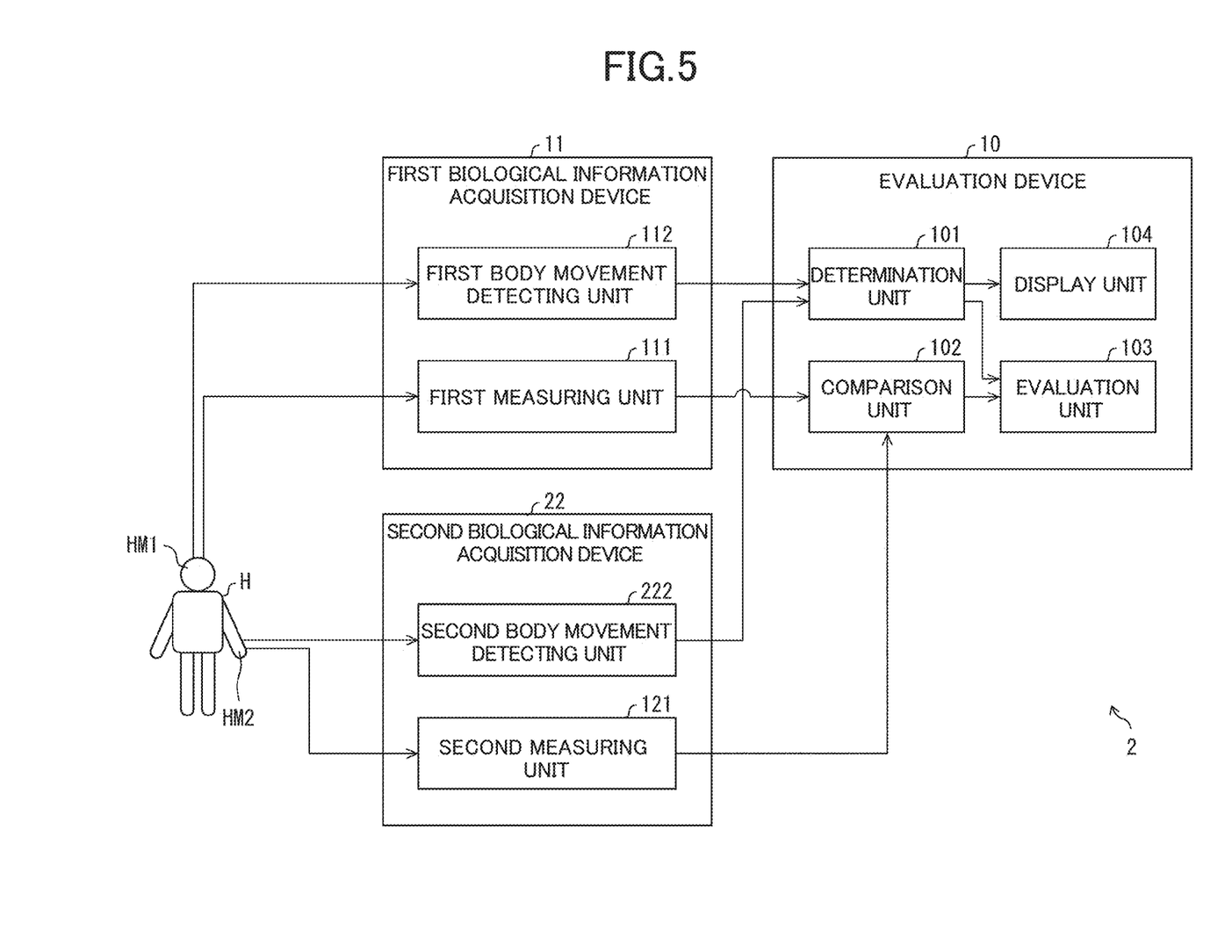
FIG. 5 is a functional block diagram illustrating a configuration of an evaluation system of Embodiment 2.

FIG. 5 is a functional block diagram illustrating a configuration of a main part of an evaluation system 2 of Embodiment 2. A second biological information acquisition device of Embodiment 2 is referred to as a second biological information acquisition device 22 (second device). For example, the second biological information acquisition device 22 is a biological information acquisition device of the contact type, similarly to the second biological information acquisition device 12. Differently from the second biological information acquisition device 12, the second biological information acquisition device 22 further includes a second body movement detecting unit 222.

For convenience, a case where the second body movement detecting unit 222 is provided in the second biological information acquisition device 22 is exemplified in Embodiment 2. Note that the second body movement detecting unit 222 may be provided outside of the second biological information acquisition device 22. It is sufficient that the second body movement detecting unit 222 is provided as a component of the evaluation system 2.

The second body movement detecting unit 222 detects a second body movement amount (hereinafter, D2) indicating the magnitude of the body movement of the second region HM2. For example, the second body movement detecting unit 222 detects D2 in a contact manner. For example, the second biological information acquisition device 22 is provided with an acceleration sensor which is not illustrated. The second body movement detecting unit 222 detects D2 by analyzing a detection result from the acceleration sensor. Alternatively, the second body movement detecting unit 222 may detect D2 by analyzing M2.

Note that, as described above, the second biological information acquisition device 22 may be a biological information acquisition device of the non-contact type. In this case, the second body movement detecting unit 222 may detect D2 in a non-contact manner. For example, the second body movement detecting unit 222 detects D2 by a method (e.g., analysis of a moving image) which is similar to that of the first body movement detecting unit 112.

In Embodiment 2, the determination unit 101 further compares D2 and a given second threshold (hereinafter, TH2) in a magnitude relationship. The determination unit 101 controls the evaluation unit 103 additionally on the basis of the magnitude relationship. When, for example, D2>TH2 is satisfied (when the second body movement amount is larger than the second threshold), the body movement of the second region HM2 is considered to be relatively great. That is, there is a concern that accuracy of M2 is not necessarily high. Then, also when D2>TH2 is satisfied, the determination unit 101 regards the evaluation result from the evaluation unit 103 as invalid.

In Embodiment 2, when (i) D1≤TH1 is satisfied and (ii) D2≤TH2 is satisfied (when the second body movement amount is smaller than or equal to the second threshold), the determination unit 101 regards the evaluation result from the evaluation unit 103 as valid. That is, in Embodiment 2, a condition of "D1≤TH1 and D2≤TH2" is set as the body movement condition.

According to the evaluation system 2, it is possible to determine the validity of the evaluation result from the evaluation unit 103 by further considering D2. Accordingly, for example, it is possible to decide, by further considering D2, whether or not to cause the evaluation unit 103 to perform evaluation. Specifically, it is possible to cause the evaluation unit 103 to perform evaluation only when the body movement of both the first region HM1 and the second region HM2 is small. Therefore, it is possible to further improve the reliability of the evaluation result of the first biological information acquisition device 11.

Embodiment 3

Figure 6:
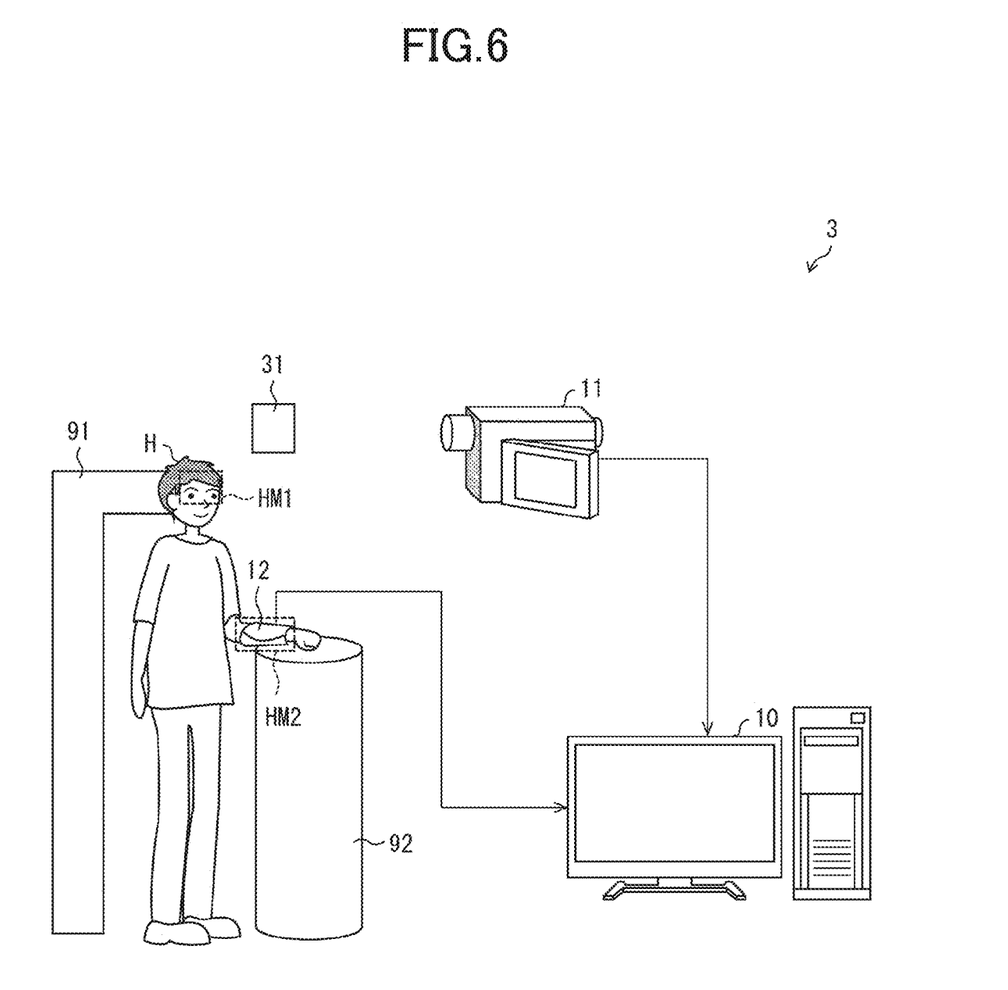
FIG. 6 is a view illustrating an outline of an evaluation system of Embodiment 3.

FIG. 6 is a view illustrating an outline of an evaluation system 3 of Embodiment 3. Differently from the evaluation system 1, the evaluation system 3 further includes a light detection unit 31. The light detection unit 31 is a known optical sensor. The light detection unit 31 detects a state of light (condition of light) in the first region HM1. The light detection unit 31 is arranged in a vicinity of the first region HM1.

For example, the state of the light may be represented by an element of (i) a light amount of the light in the first region HM1, (ii) an optical spectrum of the light in the first region HM1, or the like. For simplification, a case where the state of the light is represented only by the light amount of the light in the first region HM1 is exemplified in Embodiment 3.

As described above, a case where the first biological information acquisition device 11 acquires M1 by analyzing the moving image is considered. In this case, there is a preferable range for brightness of the image of the face included in the moving image.

When, for example, the brightness of the image of the face included in the moving image is too low, the accuracy in measuring M1 may be lowered. Accordingly, it is preferable that the light amount of the light in the first region HM1 not be too small. On the other hand, also when the brightness of the image of the face included in the moving image is too high, the accuracy in measuring M1 may be lowered. Accordingly, it is also preferable that the light amount of the light in the first region HM1 is not too large.

Then, in Embodiment 3, the determination unit 101 controls the evaluation unit 103 additionally on the basis of the state of the light which is detected by the light detection unit 31. For example, the light amount of the light detected by the light detection unit 31 is represented as LS. Moreover, two thresholds related to LS are referred to as THL1 and THL2. Note that THL1<THL2 is satisfied. That is, THL1 is a smaller threshold related to LS and THL2 is a greater threshold related to LS.

When, for example, LS<THL1 is satisfied, the light amount of the light in the first region HM1 is considered to be too small to acquire highly accurate M1. Then, also when LS<THL1 is satisfied, the determination unit 101 regards the evaluation result from the evaluation unit 103 as invalid.

On the other hand, when LS>THL2 is satisfied, the light amount of the light in the first region HM1 is considered to be too large to acquire highly accurate M1. Then, also when LS>THL2 is satisfied, the determination unit 101 regards the evaluation result from the evaluation unit 103 as invalid. As above, also when the state of the light does not satisfy a predetermined condition (specifically, a condition of "THL1≤LS≤THL2"), the determination unit 101 regards the evaluation result from the evaluation unit 103 as invalid. Hereinafter, the predetermined condition related to the state of the light is also referred to as a light condition. When, for example, the light condition is not satisfied, the determination unit 101 does not permit the evaluation unit 103 to perform evaluation, regardless of whether or not the body movement condition is satisfied.

In Embodiment 3, when (i) D1≤TH1 is satisfied and (ii) THL1≤LS≤THL2 is satisfied, the determination unit 101 regards the evaluation result from the evaluation unit 103 as valid. When, for example, both the light condition and the body movement condition are satisfied, the determination unit 101 permits the evaluation unit 103 to perform evaluation. According to a configuration of Embodiment 3, it is possible to determine the validity of the evaluation result from the evaluation unit 103 by further considering the state of the light in the first region HM1. Accordingly, for example, by further considering the state of the light, it is possible to decide whether or not to cause the evaluation unit 103 to perform evaluation. That is, it is possible to set a common reference condition (light condition) additionally for the state of the light. Therefore, it is possible to further improve the reliability of the evaluation result of the first biological information acquisition device 11.

Modified Example

Figure 7:
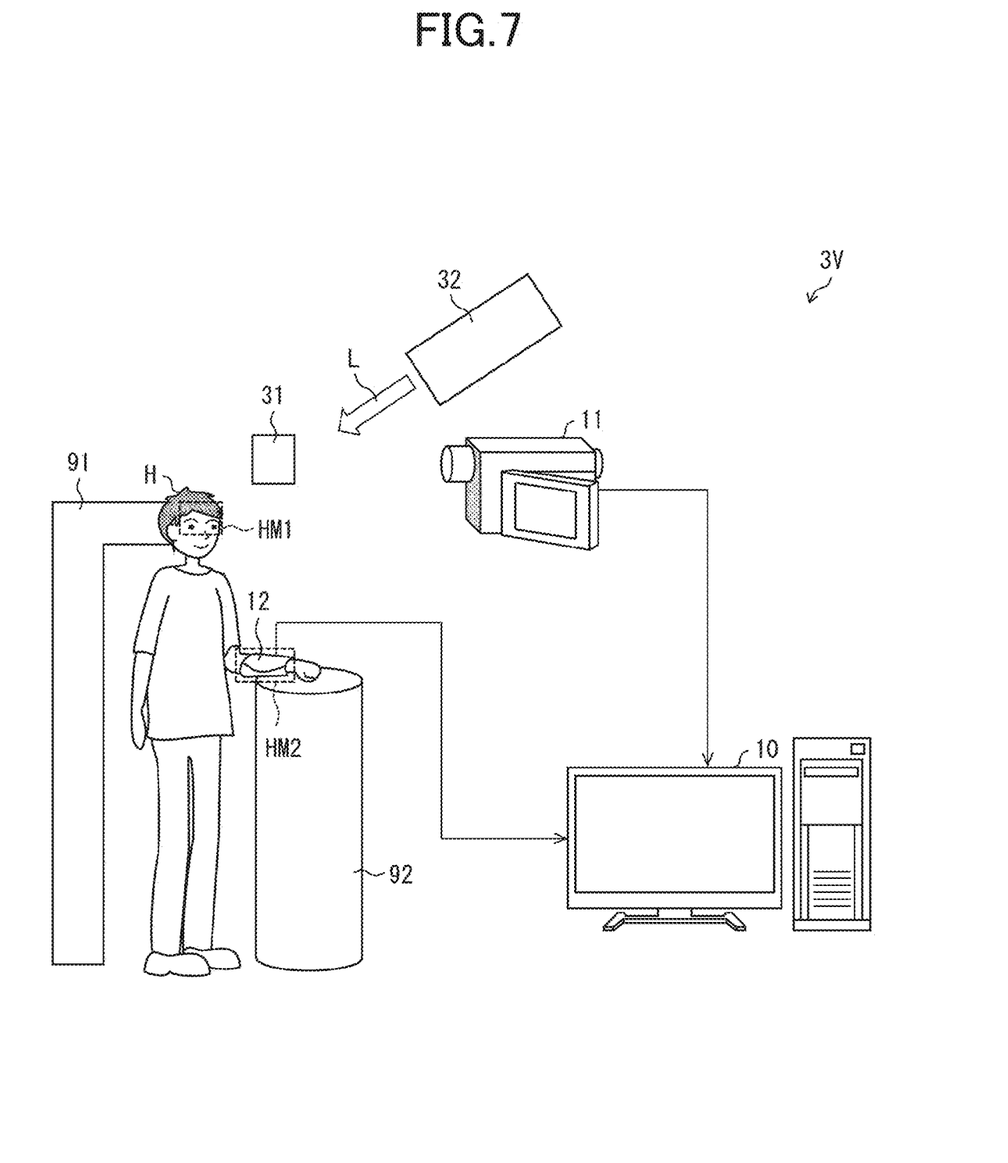
FIG. 7 is a view illustrating an outline of the evaluation system of FIG. 6 of a modified example.

FIG. 7 is a view illustrating an outline of an evaluation system 3V which is a modified example of the evaluation system 3. Differently from the evaluation system 3, the evaluation system 3V further includes a light source 32. The light source 32 emits illumination light L toward the first region HM1. For example, the light source 32 may be controlled by the evaluation device 10.

In the example of FIG. 7, the light source 32 is provided as a member separated from the first biological information acquisition device 11. However, the light source 32 may be included in the first biological information acquisition device 11. Note that the evaluation system 3V may further include a member (light source fixation member) which fixes the light source 32.

For example, upon an order of the evaluation device 10, the light source 32 changes brightness of the illumination light L. Therefore, the light source 32 is able to emit the illumination light L to the first region HM1 so as to make the state of the light in the first region HM1 conform to the light condition. When, for example, LS<THL1 is satisfied, upon an order of the evaluation device 10, the light source 32 increases the brightness of the illumination light L. Alternatively, when LS>THL2 is satisfied, upon an order of the evaluation unit 10, the light source 32 decreases the brightness of the illumination light L.

In this manner, by providing the light source 32, it is possible to change the state of the light in the first region HM1 so as to satisfy the light condition. Therefore, it is possible to more reliably achieve the state of the light which is suitable for measurement performed by the first biological information acquisition device 11. That is, it is possible to improve convenience of a measurement system.

Embodiment 4

Figure 8:
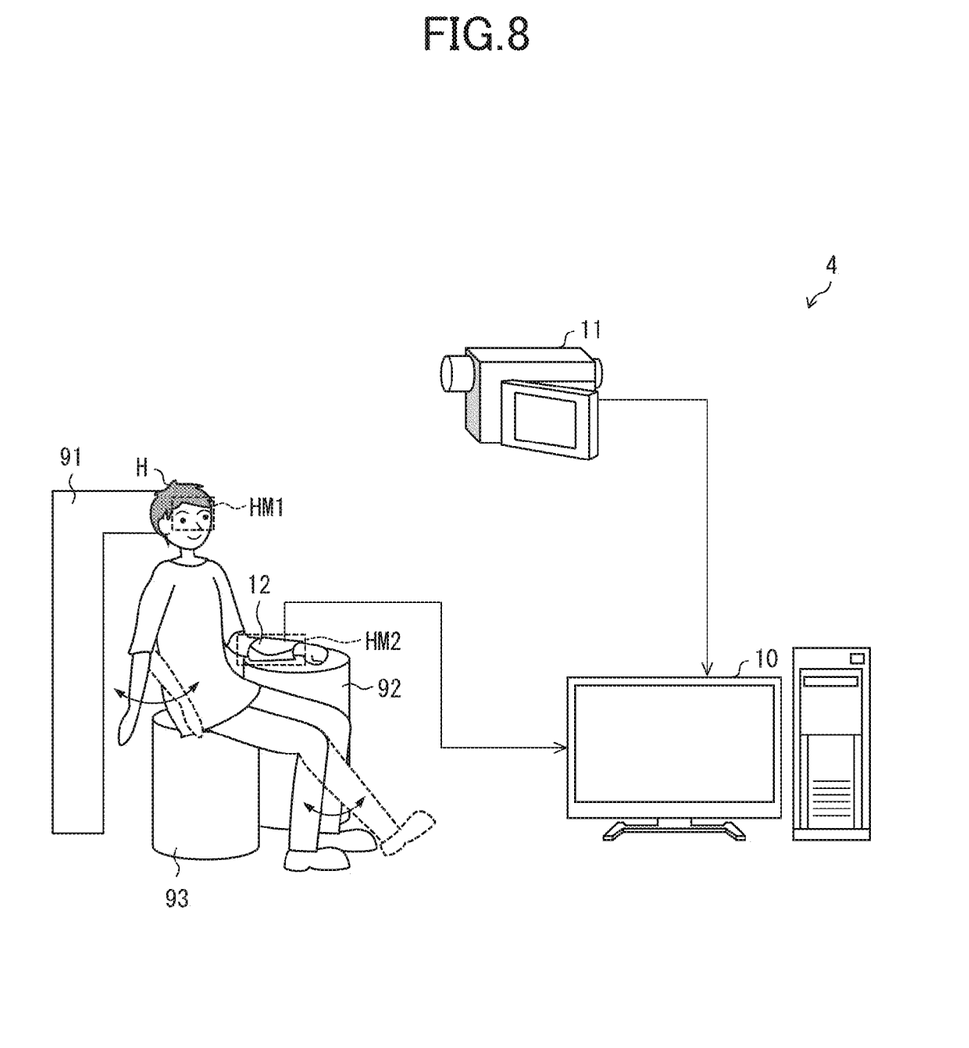
FIG. 8 is a view illustrating an outline of an evaluation system of Embodiment 4.

FIG. 8 is a view illustrating an outline of an evaluation system 4 of Embodiment 4. Differently from the evaluation system 1, the evaluation system 4 further includes a stool 93 (third body movement suppressing unit). The stool 93 includes a seat surface on which the subject H is able to be seated. The stool 93 supports buttocks of the subject H by the seat surface. In Embodiment 4, the first region HM1 is either the face or the neck of the subject H. In an example of FIG. 8, the first region HM1 is the face of the subject H.

When the biological information is acquired in the evaluation system 4, for example, upon an instruction by the evaluation system 4, the subject H who is seated on the stool 93 moves at least one of a right arm (arm of two arms, which is different from the second region HM2) and a right leg (leg of two legs, which corresponds to the right arm). Moreover, the subject H may further move a left leg. In the example of FIG. 8, the subject H moves the right arm and the right leg so as to swing.

In this manner, in Embodiment 4, the biological information is acquired in a state where the subject H moves at least one of the right arm, the right leg, and the left leg. Accordingly, it is possible to change a measurement condition of the biological information while the body movement in the first region HM1 and the second region HM2 is suppressed. Therefore, it is possible to acquire the biological information under more various measurement conditions. Thus, it is possible to evaluate the first biological information acquisition device 11 in various perspectives.

Note that it is preferable that at least some of the first biological information acquisition device 11, the first body movement suppressing unit 91, the second body movement suppressing unit 92, and the stool 93 be placed on the same placement surface (e.g., a floor in a room). With this configuration, a relative positional relationship of the respective members is easily and stably kept, so that it is possible to enhance the reliability of the evaluation result of the first biological information acquisition device 11.

Moreover, instead of the stool 93, a bed is also able to be used as the third body movement suppressing unit. In addition, the placement surface (e.g., the floor) itself is also able to be used as the third body movement suppressing unit. Furthermore, also by bringing at least one of the first region HM1 (e.g., the face of the subject H) and the second region HM2 (e.g., the left arm of the subject H) into contact with the third body movement suppressing unit (e.g., the bed or the placement surface), it is possible to stably hold each region. That is, the third body movement suppressing unit is able to be used additionally as at least one of the first body movement suppressing unit and the second body movement suppressing unit.

[Implementation Example by Software]

A control block (particularly, the evaluation device 10) of each of the evaluation systems 1 to 4 may be implemented by a logic circuit (hardware) formed in an integrated circuit (IC chip) or the like or may be implemented by software.

In the latter case, each of the evaluation systems 1 to 4 includes a computer that executes a command of a program that is software implementing each function. The computer includes, for example, at least one processor (control device) and at least one computer-readable recording medium that stores the program. When the processor reads the program from the recording medium and executes the program in the computer, an object of an aspect of the present disclosure is achieved. As the processor, for example, a Central Processing Unit (CPU) is able to be used. As the recording medium, a "non-transitory tangible medium" such as a tape, a disk, a card, a semiconductor memory, or a programmable logic circuit is able to be used in addition to a Read Only Memory (ROM) and the like. Moreover, a Random Access Memory (RAM), which develops the program, or the like may be further included. Further, the program may be supplied to the computer via any transmission medium (such as a communication network or a broadcast wave) which allows the program to be transmitted. Note that an aspect of the present disclosure can also be implemented in a form of a data signal in which the program is embodied through electronic transmission and which is embedded in a carrier wave.

[Additional Notes]

An aspect of the present disclosure is not limited to each of the embodiments described above and may be modified in various manners within the scope indicated in the claims, and an embodiment achieved by appropriately combining technical means disclosed in each of different embodiments is also encompassed in the technical scope of an aspect of the present disclosure. Further, by combining the technical means disclosed in each of the embodiments, a new technical feature may be formed.

CROSS-REFERENCE OF RELATED APPLICATION

The present application claims benefits of priority based on Japanese Patent Application No. 2018-053225 filed on Mar. 20, 2018, the entire content of which is incorporated herein by reference.

REFERENCE SIGNS LIST 1, 2, 3, 3V, 4 evaluation system
10 evaluation device
11 first biological information acquisition device (first device)
12, 22 second biological information acquisition device (second device)
31 light detection unit 132 light source
91, 91a to 91d first body movement suppressing unit
92 second body movement suppressing unit
101 determination unit (evaluation determination unit)
102 comparison unit
103 evaluation unit
104 display unit
112 first body movement detecting unit
222 second body movement detecting unit
H subject (living body)
HM1 first region
HM2 second region
TH1 first threshold
TH2 second threshold
D1 first body movement amount D2 second body movement amount
M1 first measurement value
M2 second measurement value
L illumination light
R comparison result (result of comparison of comparison unit)

The invention claimed is:

1. An evaluation system evaluating a first device that is a biological information acquisition device of a non-contact type,
the first device acquiring a first measurement value, which indicates biological information of a living body, by measuring a first region of the living body in a non-contact manner,
the evaluation system comprising:
a first body movement suppressing unit that suppresses body movement of the first region;
a first body movement detecting unit that detects a first body movement amount, which indicates a magnitude of the body movement of the first region, in the non-contact manner;
a second device that is a biological information acquisition device different from the first device,
the second device acquiring a second measurement value, which indicates the biological information, by measuring a second region of the living body;
a comparison unit that compares the first measurement value and the second measurement value;
an evaluation unit that evaluates the first device based on a result of the comparison of the comparison unit; and
an evaluation determination unit that, in a case where the first body movement amount is equal to or less than a first threshold, outputs validity information which indicates that an evaluation result of the first device from the evaluation unit is valid.

2. The evaluation system according to claim 1, wherein at least a part of a period during which the first device acquires the first measurement value overlaps a period during which the second device acquires the second measurement value.

3. The evaluation system according to claim 2, wherein all of the period during which the first device acquires the first measurement value overlaps the period during which the second device acquires the second measurement value.

4. The evaluation system according to claim 3, further comprising a second body movement suppressing unit that suppresses body movement of the second region.

5. The evaluation system according to claim 3, further comprising
a second body movement detecting unit that detects a second body movement amount which indicates magnitude of body movement of the second region, wherein
the evaluation determination unit outputs the validity information, when (i) the first body movement amount is equal to or less than the first threshold and (ii) the second body movement amount is equal to or less than a second threshold.

6. The evaluation system according to claim 3, further comprising
a light detection unit that detects a state of light in the first region, wherein
when the state of the light does not satisfy a predetermined light condition, the evaluation determination unit outputs invalidity information which indicates that the evaluation result of the first device from the evaluation unit is invalid.

7. The evaluation system according to claim 2, further comprising a second body movement suppressing unit that suppresses body movement of the second region.

8. The evaluation system according to claim 2, further comprising
a second body movement detecting unit that detects a second body movement amount which indicates magnitude of body movement of the second region, wherein
the evaluation determination unit outputs the validity information, when (i) the first body movement amount is equal to or less than the first threshold and (ii) the second body movement amount is equal to or less than a second threshold.

9. The evaluation system according to claim 2, further comprising
a light detection unit that detects a state of light in the first region, wherein
when the state of the light does not satisfy a predetermined light condition, the evaluation determination unit outputs invalidity information which indicates that the evaluation result of the first device from the evaluation unit is invalid.

10. The evaluation system according to claim 1, further comprising a second body movement suppressing unit that suppresses body movement of the second region.

11. The evaluation system according to claim 10, further comprising
a second body movement detecting unit that detects a second body movement amount which indicates magnitude of body movement of the second region, wherein
the evaluation determination unit outputs the validity information, when (i) the first body movement amount is equal to or less than the first threshold and (ii) the second body movement amount is equal to or less than a second threshold.

12. The evaluation system according to claim 10, further comprising
a light detection unit that detects a state of light in the first region, wherein
when the state of the light does not satisfy a predetermined light condition, the evaluation determination unit outputs invalidity information which indicates that the evaluation result of the first device from the evaluation unit is invalid.

13. The evaluation system according to claim 1, further comprising
a second body movement detecting unit that detects a second body movement amount which indicates magnitude of body movement of the second region, wherein
the evaluation determination unit outputs the validity information, when (i) the first body movement amount is equal to or less than the first threshold and (ii) the second body movement amount is equal to or less than a second threshold.

14. The evaluation system according to claim 1, further comprising
a light detection unit that detects a state of light in the first region, wherein
when the state of the light does not satisfy a predetermined light condition, the evaluation determination unit outputs invalidity information which indicates that the evaluation result of the first device from the evaluation unit is invalid.

15. The evaluation system according to claim 14, further comprising a light source that emits illumination light to the first region so as to make the state of the light conform to the light condition.

16. The evaluation system according to claim 1, wherein
the second device acquires the second measurement value by measuring the second region in a non-contact manner, and
the first region and the second region are in an identical region.

17. The evaluation system according to claim 1, further comprising
a second body movement detecting unit that detects a second body movement amount which indicates magnitude of body movement of the second region, wherein
the second device acquires the second measurement value by measuring the second region in a contact manner, and
the second body movement detecting unit detects the second body movement amount in the contact manner.

18. The evaluation system according to claim 1, further comprising
a display unit, wherein
the evaluation determination unit outputs, to the display unit, invalidity information, which indicates that the evaluation result of the first device from the evaluation unit is invalid, when the first body movement amount is larger than the first threshold, and
the display unit displays the invalidity information.

19. A biological information acquisition device of a non-contact type, which is determined, by the evaluation system according to claim 1, to satisfy predetermined performance.

20. An evaluation device included in an evaluation system evaluating a first device that is a biological information acquisition device of a non-contact type,
the first device acquiring a first measurement value, which indicates biological information of a living body, by measuring a first region of the living body in a non-contact manner,
the evaluation system further including
a first body movement suppressing unit that suppresses body movement of the first region,
a first body movement detecting unit that detects a first body movement amount, which indicates a magnitude of the body movement of the first region, in the non-contact manner, and
a second device that is a biological information acquisition device different from the first device,
the second device acquiring, in the evaluation system, a second measurement value, which indicates the biological information, by measuring a second region of the living body,
the evaluation device comprising:
a comparison unit that compares the first measurement value and the second measurement value;
an evaluation unit that evaluates the first device based on a result of the comparison of the comparison unit; and
an evaluation determination unit that, in a case where the first body movement amount is equal to or less than a first threshold, outputs validity information which indicates that an evaluation result of the first device from the evaluation unit is valid.

* * * * *